United States Patent
Stangelmayer

(10) Patent No.: US 9,759,660 B2
(45) Date of Patent: Sep. 12, 2017

(54) SENSOR ASSEMBLY, METHOD, AND MEASURING SYSTEM FOR CAPTURING THE DISTRIBUTION OF AT LEAST ONE VARIABLE OF AN OBJECT

(75) Inventor: Achim Stangelmayer, Neuburg (DE)

(73) Assignee: PreSens—Precision Sensing GmbH, Regensburg (DE)

( * ) Notice: Subject to any disclaimer, the term of this patent is extended or adjusted under 35 U.S.C. 154(b) by 1326 days.

(21) Appl. No.: 13/310,975

(22) Filed: Dec. 5, 2011

(65) Prior Publication Data
US 2012/0145882 A1   Jun. 14, 2012

Related U.S. Application Data

(60) Provisional application No. 61/459,463, filed on Dec. 13, 2010.

(30) Foreign Application Priority Data

Dec. 13, 2010   (DE) .................. 10 2010 061 182

(51) Int. Cl.
*G01N 21/64*   (2006.01)

(52) U.S. Cl.
CPC ..... *G01N 21/6456* (2013.01); *G01N 21/6408* (2013.01)

(58) Field of Classification Search
CPC .................. G01N 21/63; G01N 21/64; G01N 2021/6419; G01N 2021/6421
USPC ............... 250/208.1, 216, 222.1, 226, 214.1, 250/559.28, 239; 356/39, 40; 348/294–312; 257/431–440
See application file for complete search history.

(56) References Cited

U.S. PATENT DOCUMENTS

| | | | |
|---|---|---|---|
| 5,546,209 A * | 8/1996 | Willner et al. .................. | 398/43 |
| 5,591,959 A * | 1/1997 | Cigna .................. | H01L 27/146 |
| | | | 250/208.1 |
| 6,356,381 B1 * | 3/2002 | Schade et al. ................ | 359/326 |
| 6,379,969 B1 * | 4/2002 | Mauze ............... | G01N 21/6428 |
| | | | 422/82.05 |

(Continued)

FOREIGN PATENT DOCUMENTS

| DE | 10 2005 036 410 | 2/2007 |
|---|---|---|
| EP | 1 130 382 | 9/2001 |

(Continued)

OTHER PUBLICATIONS

"Functional and structural imaging of phototrophic microbial communities and symbioses" by Michael Kühl and Lubos Polerecky, Aquat Microb Ecol 53 (2008), 99, doi 10.3354/ame01224.

*Primary Examiner* — Francis M Legasse, Jr.
*Assistant Examiner* — Don Williams
(74) *Attorney, Agent, or Firm* — Davidson, Davidson & Kappel, LLC

(57) ABSTRACT

A sensor assembly, a method, and a measuring system for capturing the distribution of at least one variable of an object are disclosed. The sensor assembly has at least one sensor element comprising at least one first sensor sub-element and at least one second sensor sub-element. The at least one first sensor sub-element is transparent for at least one wavelength region of light, the at least one second sensor sub-element is sensitive to at least one variable. Furthermore a method and measuring system and an illumination system for illuminating the sensor assembly and the object is provided.

28 Claims, 6 Drawing Sheets

(56) References Cited

U.S. PATENT DOCUMENTS

| | | |
|---|---|---|
| 6,414,746 B1* | 7/2002 | Stettner et al. .............. 356/4.01 |
| 2004/0171094 A1 | 9/2004 | Klimant et al. .................. 435/8 |
| 2005/0253087 A1 | 11/2005 | Plan .......................... 250/458.1 |
| 2008/0095298 A1* | 4/2008 | Shefsky ............................ 378/2 |
| 2008/0272313 A1* | 11/2008 | Van Herpen ....... G01N 21/6428 |
| | | 250/459.1 |
| 2009/0146080 A1 | 6/2009 | Liebsch ..................... 250/484.4 |
| 2009/0302407 A1 | 12/2009 | Gidon et al. .................. 257/432 |
| 2011/0240471 A1* | 10/2011 | Wheeler ........... B01L 3/502784 |
| | | 204/451 |

FOREIGN PATENT DOCUMENTS

| | | |
|---|---|---|
| EP | 1 414 336 | 5/2004 |
| WO | WO 01/50101 | 7/2001 |
| WO | WO 02/056023 | 7/2002 |
| WO | WO 02/103334 | 12/2002 |

* cited by examiner

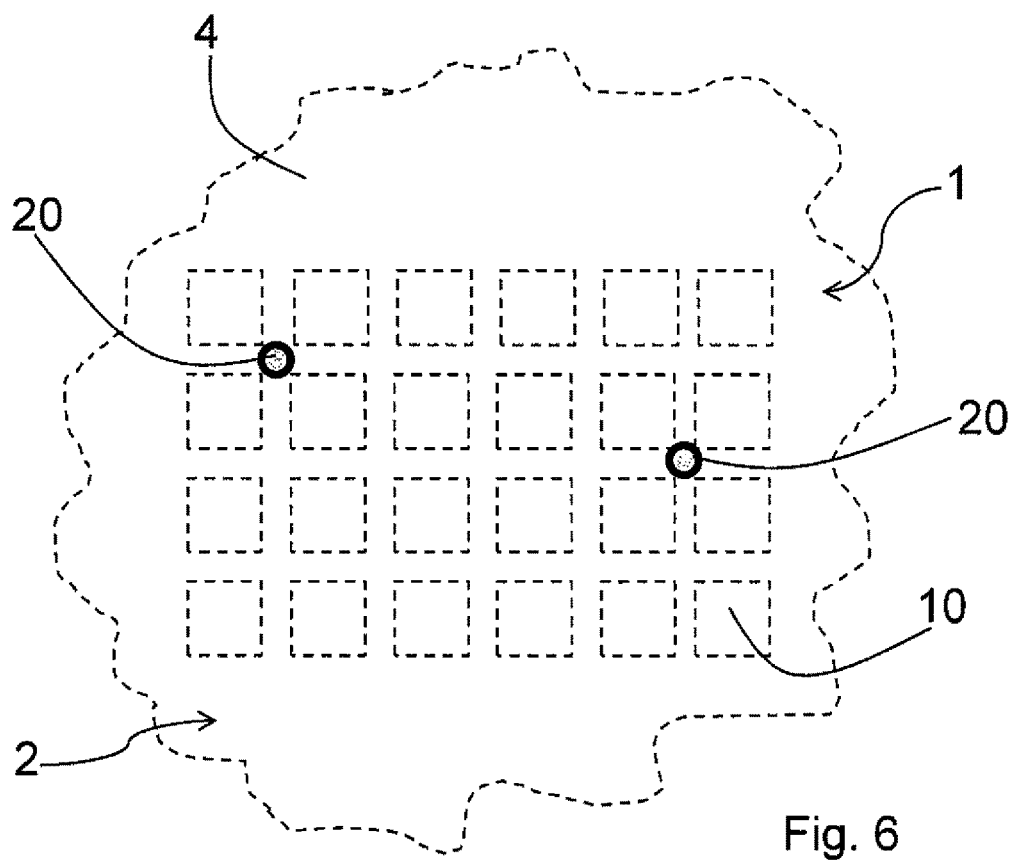
Fig. 6
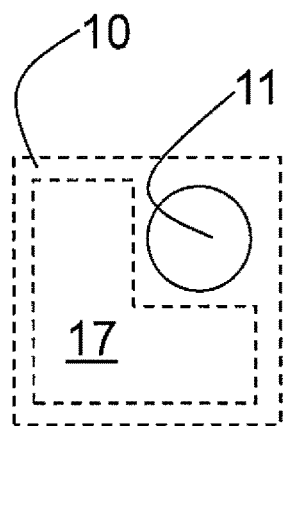
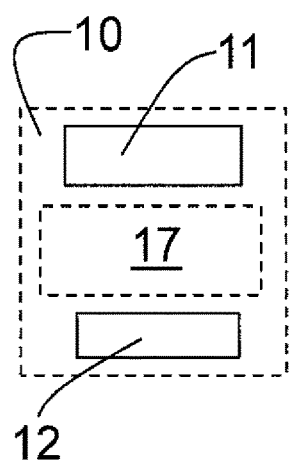
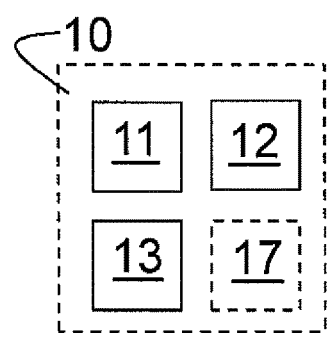
Fig. 7a                Fig. 7b                Fig. 7c

SENSOR ASSEMBLY, METHOD, AND MEASURING SYSTEM FOR CAPTURING THE DISTRIBUTION OF AT LEAST ONE VARIABLE OF AN OBJECT

This claims the benefit of German Patent Application No. 10 2010 061 182.4, filed on Dec. 13, 2010 and of U.S. Provisional Patent Application 61/459,463 filed on Dec. 13, 2010, both of which are hereby incorporated by reference herein.

FIELD OF THE INVENTION

The present invention relates to a sensor assembly for capturing the distribution of at least one variable of an object, as well as a corresponding method and a corresponding measuring system. In particular, the invention relates to a sensor assembly, a method, and a measuring system by which the distribution of the at least one variable can be captured in an image-like fashion.

BACKGROUND

The German patent application DE 10 2005 036 410 A1 discloses a method for determining the distribution of the partial pressure of oxygen in at least one portion of a tissue surface. For this purpose a fluorescent dye is applied on the portion of the tissue surface, and is illuminated with excitation light in order to excite fluorescence. During the fluorescence build-up phase at least one first fluorescence image is recorded by means of a camera system, and in the decay phase at least one second fluorescence image is recorded by means of a camera system. Subsequently the fluorescence intensities in the build-up and decay phases are determined from the recorded first and second fluorescence images and the distribution of the oxygen partial pressure in the at least one portion of the tissue surface is found by forming the ratio of the determined fluorescence intensities.

The article "Functional and structural imaging of phototrophic microbial communities and symbioses" by Michael Kühl and Lubos Polerecky, Aquat Microb Ecol 53 (2008), 99, doi 10.3354/ame01224, describes the imaging of a cell community with simultaneous representation of the oxygen distribution by a transparent sensor. The transparent sensor therein is applied as a homogeneous layer on a carrier.

In examining objects like tissue samples with respect to the distribution of a substance contained therein it is advantageous to show the tissue sample and the distribution of the substance in a single image. If suitable transparent sensors are available for the substance in question, like in the case of oxygen mentioned above, an image can be captured through the sensor. Such transparent sensors, however, are not available for all interesting substances.

The international patent application WO 2002/056023 A1 discloses an optical sensor for determining at least one parameter in a sample. The sensor contains an indicator material sensitive to the parameter with a short decay time, and a reference material not sensitive to the parameter with a long decay time, and serves for capturing a measurement signal indicating the parameter to be determined. The measurement is based on luminescence responses of both the indicator and the reference material captured together. The indicator and the reference material are immobilised on a common carrier.

The international patent application WO 2002/103334 A1 relates to a sensor type in which microtitre plates or carriers with recesses for holding samples, are used to measure oxygen. Luminescent or fluorescent dyes (for example platinum, palladium, or ruthenium complexes with phenanthroline, porphyrine, or pyridine ligands) are contained in the wells of the microtitre plates, wherein the dyes are embedded in particles of a matrix permeable for gas but impermeable for water. The matrix is a derivative of polystyrene or a polystyrene copolymer. The particles in turn are dispersed in a second matrix permeable for water, which comprises a hydrophilic polymer, like for example polyhydroxymethacrylate, polyvinyl alcohol, or polyvinylpyrrolidone.

The European patent EP 1 414 336 B1 serves for the visualisation of fluorescent dyes for fluorescence diagnostics of, for example, tumours in humans, and is also particularly suited for a highly sensitive, quantitative early detection of a plurality of precancerous/dysplastic mutations. A digital camera system with a 3-CCD-chip (also RGB chip) is provided as optoelectric image converter. A control electronics is provided for a pulsed light source, generating the excitation light.

The European patent EP 1 130 382 B1 discloses an apparatus for analysing multiple parameters in a liquid simultaneously. The apparatus comprises a plurality of sensors, a light source for providing the light, in order to excite the sensors. Each sensor of each group has a different chemical, interacting specifically with the parameter. The differences with respect to the sensors lead to differences with respect to the light-interaction.

SUMMARY OF THE INVENTION

It is an object of the invention to provide a sensor assembly by which the distribution of at least one variable of an object can be represented in an image-like fashion, wherein a representation of the object within the same image shall be possible in order to establish a correspondence between positions in the distribution and positions on the object.

The present invention provides a sensor assembly for capturing the distribution of at least one variable of an object in an image-like fashion. The sensor assembly has at least two corresponding sensor sub-elements exhibiting fixed positions with respect to the sensor assembly. At least one first sensor sub-element is transparent for at least one wavelength region of light, and wherein at least one second sensor sub-element is sensitive to at least one variable.

A further object of the invention is to provide a method by which the distribution of at least one variable of an object can be represented in an image-like fashion, wherein a representation of the object within the same image shall be possible in order to establish a correspondence between positions in the distribution and positions on the object.

The present invention also provides a method for capturing the two-dimensional distribution of at least one variable of an object in an image-like fashion, comprising the following steps:
a) applying a sensor assembly on a surface of the object, wherein the sensor assembly has a plurality of sensor elements arranged in a matrix-like fashion, and wherein each sensor element exhibits at least one first sensor sub-element transparent for at least one wavelength region of light, and exhibits at least one second sensor sub-element, which is sensitive to at least one variable;
b) illuminating the sensor assembly with light from at least one wavelength region of light;

c) recording at least one image of a sensor response of the sensor assembly to the illumination, the sensor response representing the distribution of the at least one variable;

d) recording at least one image of the surface of the object through the first sensor sub-elements; and e) generating at least one combined image from the images recorded in the steps c and d.

An additional object of the invention is to provide a measuring system by which the distribution of at least one variable of an object can be represented in an image-like fashion, wherein a representation of the object within the same image shall be possible in order to establish a correspondence between positions in the distribution and positions on the object.

The present invention also thus provides a measuring system for capturing the two-dimensional distribution of at least one variable of an object in an image-like fashion. The measuring system comprises:

a detection system;

an illumination system; and a sensor assembly with sensor elements arranged in a matrix-like fashion, wherein each sensor element exhibits at least one first sensor sub-element, transparent for at least one wavelength region of light, and exhibits at least one second sensor sub-element, which is sensitive to at least one variable, and wherein the sensor assembly is configured to be applied on the object, the sensor assembly and the object can be illuminated with light from at least one wavelength region, and the detection system is configured to record at least one image of the sensor assembly and at least one image of the object.

According to the invention a sensor assembly for capturing the distribution of at least one variable of an object in an image-like fashion has at least one sensor element comprising at least two corresponding sensor sub-elements. The sensor sub-elements are at a fixed position relative to the sensor assembly. Furthermore at least one first sensor sub-element is transparent for at least one wavelength region of light, and at least one second sensor sub-element is sensitive to at least one variable.

According to the invention an optical behavior of the at least one second sensor sub-element may be determined, wherein the optical behavior is due to the at least one variable. The optical behavior can comprise a color change of the at least one second sensor sub-element in dependence on the at least one variable, or a change of a luminescence behavior in dependence on the at least one variable. Luminescence comprises at least phosphorescence and fluorescence; a change of the luminescence behavior for example can comprise a presence or absence of the luminescence, or a change in the build-up and/or decay times of the luminescence, or a change in the color of the luminescence, in each case in dependence on the at least one variable. A sensor assembly according to the invention therein may comprise different second sensor sub-elements, which differ in the kind of optical behavior changing in dependence on the at least one variable.

In an embodiment of the sensor assembly according to the invention the at least one first sensor sub-element, i.e. the sensor sub-element transparent for at least one wavelength region of light, of the at least one sensor element is sensitive to at least one variable. As for the kind of sensitivity of the at least one first sensor sub-element the corresponding statements on the at least one second sensor sub-element apply analogously.

According to a possible embodiment of the sensor assembly according to the invention the at least one sensor element comprises at least one first sensor sub-element and at least two second sensor sub-elements, wherein the at least two second sensor sub-elements differ with respect to the at least one variable to which they are sensitive.

The at least one variable to which the at least one second sensor sub-element or in some embodiments also the at least one first sensor sub-element of a sensor element is sensitive, may be an arbitrary measurable quantity, for example the concentration or mere presence or absence of a substance, a partial pressure of a substance (oxygen, $CO_2$, $H_2S$, $SO_2$, etc), a pH-value, a temperature, or a pressure. The preceding list is not final; any variable for which a suitable sensor is available can be captured by using this sensor in the sensor assembly according to the invention.

It is advantageous, if the sensor assembly according to the invention comprises a plurality of sensor elements which are arranged regularly in rows and columns in a matrix-like fashion. The regular arrangement facilitates the systematic recording and evaluation of images.

In any case the sensor elements of the sensor assembly need to be in such a contact with the object that the sensor sub-elements of the sensor elements can react to the at least one variable to which they respectively are sensitive. If the variable for example is a temperature, a heat transfer between the sensor sub-element and the object must be possible. If the variable for example is a concentration, presence or absence, or partial pressure of a substance, a contact of the sensor sub-element with the substance of the object must be established.

According to an embodiment of the sensor assembly according to the invention the at least one sensor element is localised on a carrier. The carrier can be made of a rigid or a flexible material, it can for example be a glass or plastic plate. The carrier may in particular also be a flexible plastic sheet. The sensor elements therein may be arranged on a surface of the carrier or embedded in the carrier. The abovementioned contact between the sensor elements and the object must in any case be assured.

Preferentially the carrier material is transparent for all wavelengths of light relevant in the recording of images, and thus at least for the illumination light and for the wavelength regions of light corresponding to the luminescence and/or the occurring colors of the sensor sub-elements.

It should be noted here that for the purposes of this application the term light refers to electromagnetic radiation of any frequency.

If the at least one sensor element is localised on a carrier, an embodiment of the invention may be such that the at least one first sensor sub-element of the at least one sensor element comprises an opening or perforation in the carrier. In this way the at least one first sensor sub-element is transparent for the wavelength regions of light used in measuring.

Alternatively, the at least one first sensor sub-element of the at least one sensor element can be made of a material transparent for the at least one wavelength region of light used in measuring. It can for example be a filter transmissive for the at least one wavelength region of light. It is also possible that the at least one first sensor sub-element of the at least one sensor element is formed in such a manner that a region of the carrier corresponding to the at least one second sensor sub-element of the at least one sensor element is left uncovered. This means that in this region no other sensor sub-element is provided. In this case the carrier, at least in the uncovered region, must be made of a material transparent for the at least one wavelength region of light.

The sensor elements of the sensor assembly according to the invention, in a different embodiment, may also be applied on the object without a carrier. For example, the sensor sub-elements may be applied on the object in droplets according to the mode of operation of an ink-jet printer. In the same way the sensor sub-elements could also be applied on a carrier. If the sensor elements are applied on the object without a carrier, in embodiments the at least one first sensor sub-element of the at least one sensor element may be a region, corresponding to the at least one second sensor sub-element of the at least one sensor element, left bare during the application of the at least one sensor element onto a surface of the object.

According to an embodiment of the sensor assembly according to the invention at least two sensor elements differ with respect to their respective sensor sub-elements. The differences between the sensor sub-elements may for example be that one sensor element exhibits a sensor sub-element sensitive to a particular variable, whereas a further sensor element does not exhibit a sensor sub-element sensitive to this particular variable. So it may for example be the case that in a sensor assembly there is only one second sensor sub-element sensitive to a temperature, whereas all other second sensor sub-elements for example are sensitive to a concentration of a substance. Further possible combinations of this kind are possible.

It is also possible for two sensor elements each to comprise a sensor sub-element sensitive to a common variable, wherein these sensor sub-elements differ with respect to their sensitivity and/or the range of the values of the common variable, to which they are sensitive.

The difference of the sensor elements with respect to their sensor sub-elements can also be such that there are a first region and a second region within the sensor assembly, wherein the sensor elements of the first region differ from the sensor elements of the second region with respect to their sensor sub-elements. In this way the sensor assembly can be adapted to the study of objects for which the presence of different regions of interest is known, for example a deposited layer of sand with water above it in an aquarium. In this case, for example, the first region of the sensor assembly would be provided for being brought into contact with the layer of sand, whereas the second region of the sensor assembly would be provided for being brought into contact with the water above the sand.

In a further embodiment of the sensor assembly according to the invention different sensor elements comprise sensor sub-elements sensitive to a common variable, wherein the sensor sub-elements differ with respect to their cross-sensitivity to respectively at least one further variable. The variables involved can be determined by an evaluation of a sensor response from all these sensor sub-elements. Thus, for example, in case of two sensor sub-elements, each sensitive to oxygen, one may exhibit a dependence of its sensor response to oxygen on hydrogen sulphide, whereas the other exhibits a dependence of its sensor response to oxygen on $SO_2$.

For the evaluation of the sensor response of the sensor assembly at least one image of the sensor assembly is recorded. In order to facilitate the correct alignment of the at least one image for evaluation, preferentially reference marks are provided in the sensor assembly. These reference marks may be sensor sub-elements or separate marks in the sensor assembly.

The method according to the invention for capturing the two-dimensional distribution of at least one variable of an object is carried out as follows:

A sensor assembly is applied on a surface of the object, wherein the sensor assembly has a plurality of sensor elements arranged in a matrix-like fashion. Therein each sensor element comprises at least one first sensor sub-element transparent for at least one wavelength region of light, and at least one second sensor sub-element, which is sensitive to at least one variable. The sensor assembly therein is illuminated with light from at least one wavelength region. Depending on the measuring task and configuration of the sensor sub-elements the illumination may be done with specifically provided light sources or by ambient light, for example daylight.

At least one image of a sensor response of the sensor assembly to the illumination is recorded, the sensor response representing the distribution of the at least one variable. Furthermore at least one image of the surface of the object is recorded through the first sensor sub-elements. This is done in at least one wavelength region of light for which the first sensor sub-elements are transparent. Due to this transparency an image of the surface of the object can be recorded, even though the surface is covered by the sensor assembly. The great advantage here is that the choice of the second sensor sub-elements is not restricted to transparent configurations.

A combined image is generated from the recorded images. This combined image in embodiments is a simple superposition of the image of the surface and of the image of the sensor response, so that within a single image an immediately evident correspondence between sensor response and positions on the surface of the object results. It is also possible for the at least one image of the sensor response to be evaluated by data processing, and the results of these evaluation processes can be represented superimposed on the image of the surface of the object in an image-like fashion.

According to an embodiment of the method the sensor assembly is illuminated with a light pulse from at least one wavelength region of light, and a plurality of images of the sensor assembly are recorded in succession. The recording of images therein may start during the duration of the light pulse. In this way localised information on the build-up and/or decay behavior of the response, for example a luminescence effect, of particular sensor sub-elements to the light pulse can be obtained from the recorded images of the sensor assembly, from which conclusions on the at least one variable to which the involved sensor sub-elements are sensitive, may be derived.

According to a further embodiment of the method the sensor assembly is illuminated with a plurality of light pulses, each from at least one wavelength region of light, in succession, and for each light pulse at least one image of the sensor assembly is recorded. Here, too, recording of the images can start during the duration of a respective light pulse. The possibilities for evaluation correspond to those described above for a single light pulse. Due to the succession of the light pulses different sensor sub-elements can be excited one after the other, and in this way information on a larger number of variables or more precise information on specific variables can be obtained. The wavelength regions of light of the respective light pulses therein are to be adapted to the respective sensor sub-elements to be excited.

According to a further embodiment of the method the sensor assembly is illuminated with continuous light. In this case, the images of the sensor assembly are evaluated in a localised fashion with respect to their spectral composition and their spectral intensity distribution. Thus here it is of interest if, and if so, how strongly, a particular sensor sub-element at a specific location responds to the excitation light. In this way, too, the distribution of the at least one variable can be determined. The continuous light used for illumination may have a broad frequency spectrum, it may for example be white light, or may be taken from a narrow spectral region.

If the illumination steps and image recording steps of the respective embodiments are carried out repeatedly at different times, the time evolution of the distribution of the at least one variable can be monitored.

For the method the sensor assembly may be applied on the surface of the object by separately applying the individual sensor sub-elements onto the surface of the object, for example as with an ink-jet printer. The sensor assembly may also be applied on the surface of the object by applying a carrier exhibiting the sensor elements of the sensor assembly on the surface of the object, for example by applying a plastic sheet provided with the sensor elements on the surface of the object. According to a further possibility of applying the sensor elements on the surface of the object the sensor elements at first are provided on an intermediate medium, which is brought into contact with the surface of the object in such a way that the sensor elements stick to the surface of the object. Then the intermediate medium is removed, wherein the sensor elements detach from the intermediate medium and thus are arranged on the surface of the object.

A measuring system for capturing the two-dimensional distribution of at least one variable of an object has a detection system and an illumination system, and according to the invention furthermore has a sensor assembly with sensor elements arranged in a matrix-like fashion, wherein each sensor element exhibits at least one first sensor sub-element, transparent for at least one wavelength region of light, and at least one second sensor sub-element, sensitive to at least one variable. The sensor assembly is configured to be applied on the object, sensor assembly and object can be illuminated by the illumination system with light of at least one wavelength. The detection system is configured to record at least one image of the sensor assembly and at least one image of the object.

In an embodiment of the measuring system the detection system comprises at least one detector and corresponding imaging optics, wherein each detector exhibits a sensitivity in at least one wavelength region of light. In specific embodiments light from a wavelength region where regions of sensitivity of a detector overlap is suppressed by an optical notch filter. If, for example, a detector exhibits sensitivities in the red, green, and blue regions of the visible spectrum, and if the sensitivity curves for, for example, red and green of the detector overlap in a wavelength region corresponding to the yellow region of the visible spectrum, yellow light from the respective overlap region can be suppressed by a suitably chosen notch filter.

Apart from daylight or ambient light, which are used in some embodiments of the invention, many possibilities for a suitable illumination of the sensor assembly are known to the person skilled in the art. Conventional lamps or flash lights, LEDs, OLEDs, or lasers may for example be used as light sources. Depending on the measuring task and the configuration of the sensor assembly these light sources may be combined with filters or filter systems for the illumination of the object and of the sensor assembly. The filters or filter systems therein may be configured to be switchable.

According to an embodiment of the invention the sensor assembly for capturing the distribution of at least one variable of an object in an image-like fashion has at least one sensor element. The sensor element has at least one first sensor sub-element and at least two second sensor sub-elements, wherein the at least two second sensor sub-elements differ with respect to at least one variable to which they are sensitive. The at least two corresponding sensor sub-elements exhibiting fixed positions with respect to the sensor assembly. At least one first sensor sub-element is transparent for at least one wavelength region of light. The at least two second sensor sub-element are sensitive to at least one variable.

BRIEF DESCRIPTION OF THE DRAWINGS

According to an embodiment of the measuring system according to the invention the operation of the illumination system is based on a luminescence effect. This is a particular advantage, if the luminescence occurs in a wavelength region of light particularly suited for the respective measurements.

Below the invention and its advantages are described in greater detail with reference to the accompanying figures. There are shown in FIG. 1 a schematic representation of a sensor assembly on a carrier;

FIG. 6 a schematic representation of a sensor assembly which has been applied on a surface of an object without a carrier;

FIG. 7a an embodiment of the schematic arrangement of the sensor sub-elements of a sensor element, wherein no carrier is provided;

FIG. 7b a further embodiment of the schematic arrangement of the sensor sub-elements of a sensor element, wherein no carrier is provided;

FIG. 7c a further embodiment of the schematic arrangement of the sensor sub-elements of a sensor element, wherein no carrier is provided;

DETAILED DESCRIPTION OF THE INVENTION

Figure 1:
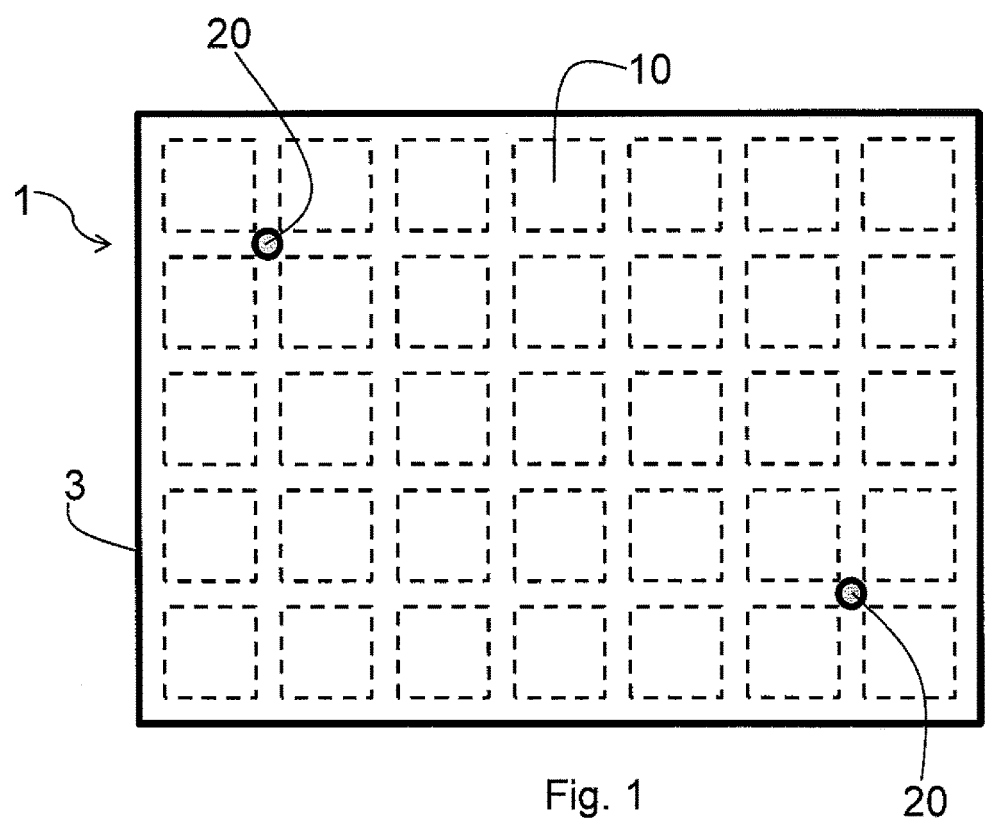

In the figures identical reference numerals have been used for like elements of the invention of elements of like function. Furthermore, for the sake of clarity, only those reference numerals are shown in the individual figures which are required for the description of the respective figure. The embodiments shown only are examples of how the sensor assembly according to the invention, the measuring system according to the invention, and the method may be realised, and are not to be taken as a limitation of the invention. The size ratios of the individual elements in the figures do not always correspond to the real size ratios, as some shapes have been shown in a simplified fashion and other shapes enlarged, for better illustration, with respect to other elements.

FIG. 1 shows a sensor assembly 1 according to the invention on a carrier 3. In this embodiment the sensor assembly 1 has a plurality of sensor elements 10 arranged regularly in rows and columns in a matrix-like fashion. The regular arrangement of the sensor elements 10 is particularly advantageous for the representation, in an image-like fashion, of the distribution of the at least one variable, the invention, however, is not limited to regular arrangements of sensor elements.

In order to facilitate the alignment of recorded images of the sensor assembly 1 during evaluation, in this embodiment of the sensor assembly two reference marks 20 are provided, which are arranged between the sensor elements. In different embodiments at least one reference mark may be part of a sensor element. Also, more than two reference marks, or only one reference mark, may be provided.

Figures 2A, 2B, 2C:
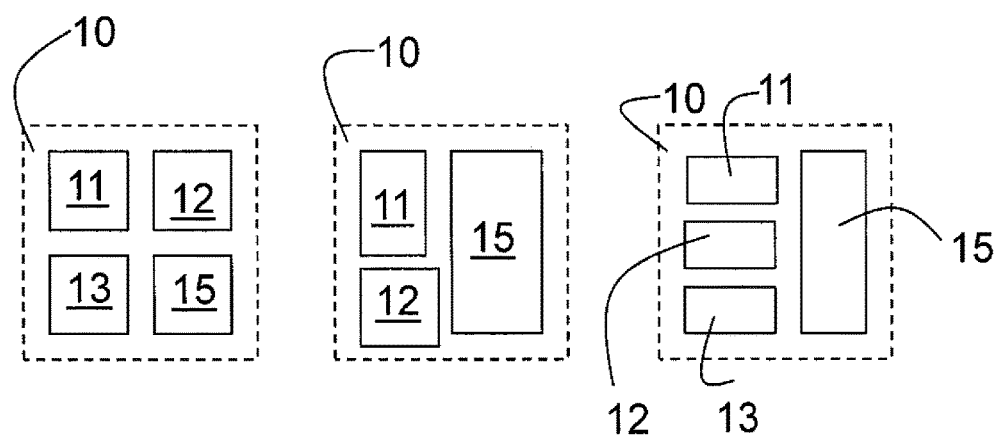
FIG. 2a an embodiment of the schematic arrangement of the sensor sub-elements of a sensor element.
FIG. 2b a further embodiment of the schematic arrangement of the sensor sub-elements of a sensor element.
FIG. 2c a further embodiment of the schematic arrangement of the sensor sub-elements of a sensor element.

FIG. 2a shows an example of a configuration of a sensor element 10 on a carrier 3 (see FIG. 1), which comprises one first sensor sub-element 15 and three second sensor sub-elements 11, 12, 13. According to the invention the first sensor sub-element 15 is transparent for at least one wavelength region of light. In embodiments it may be an optical filter, transmissive in the at least one wavelength region of light. It is also possible for the first sensor sub-element 15 to be provided as a region left uncovered on the carrier 3, wherein then the carrier 3, at least in the region of the first sensor sub-element 15, is transparent for the at least one wavelength region of light. A further possibility is for the first sensor sub-element 15 to comprise an opening in or a perforation of the carrier 3, so that the transparency of the first sensor sub-element 15 for at least one wavelength region of light or for the entire wavelength region of light used for measuring is realised.

The second sensor sub-elements 11, 12, 13 according to the invention each are sensitive to at least one variable of an object 2 (see FIGS. 3, 4, 5, 6, 8). According to an embodiment of the invention the first sensor sub-element 15, in addition to its transparency for at least one wavelength region of light, may also be sensitive to at least one variable of the object 2. Therein it is also possible for at least two sensor sub-elements 11, 12, 13, 15 to be sensitive to at least one common variable. The sensor elements 10 of a sensor assembly 1 may differ with respect to their sensor sub-elements.

The invention is not limited to a sensor element 10 comprising only one first sensor sub-element 15. Plural sensor sub-elements may be transparent each for at least one wavelength region of light.

FIG. 2b shows a further embodiment of a sensor element 10, comprising one first sensor sub-element 15 and two second sensor sub-elements 11, 12. As for the possible configurations of the first sensor sub-element 15 and of the second sensor sub-elements 11, 12 the corresponding statements made in the context of FIG. 2a apply. The example shown illustrates that the individual sensor sub-elements 11, 12, 15 of a sensor element 10 may differ with respect to size and shape. Even though the description essentially is restricted to sensor sub-elements 11, 12, 15 of a rectangular shape, this is not to be considered a limitation of the invention. The sensor sub-elements 11, 12, 15 may exhibit a large variety of shapes.

Due to the various sizes of the sensor sub-elements 11, 12, 15 specific requirements for measurements by means of the sensor assembly 1 (see FIG. 1) may be taken into account. In the case of luminescence-based second sensor sub-elements 11, 12, a larger second sensor sub-element 11, 12, for example, increases the yield of luminescence light under otherwise identical conditions, i.e. for at least the same values of the variables and identical ambient conditions. In this way properties of the materials used for the first and second sensor sub-elements 11, 12, 15 can be taken into account in the configuration of the sensor elements 10 with respect to specific measuring tasks.

FIG. 2c shows a further embodiment of a sensor element 10, with a first sensor sub-element 15 and three second sensor sub-elements 11, 12, 13. Again the first sensor sub-element 15 and the second sensor sub-elements 11, 12, 13 differ in size.

In the configuration of the sensor elements 10 with respect to the arrangement and distribution of the sensor sub-elements 11, 12, 13, 15 it needs to be considered on the one hand that no contact of the substances occurs between the individual sensor sub-elements 11, 12, 13, 15, at least not if such a contact of the substances would have a detrimental effect on the operation of the sensor element 10. On the other hand, smaller sizes of the sensor elements 10 can be realised by a particularly efficient and space-saving arrangement of the sensor sub-elements 11, 12, 13, 15 in a sensor element 10. In this way, for a given total area of the sensor assembly 1 (see FIG. 1), a higher spatial resolution of the distribution of the at least one variable can be achieved. It is quite possible for the sensor elements 10 of a sensor assembly 1 to differ in size.

Figure 3:
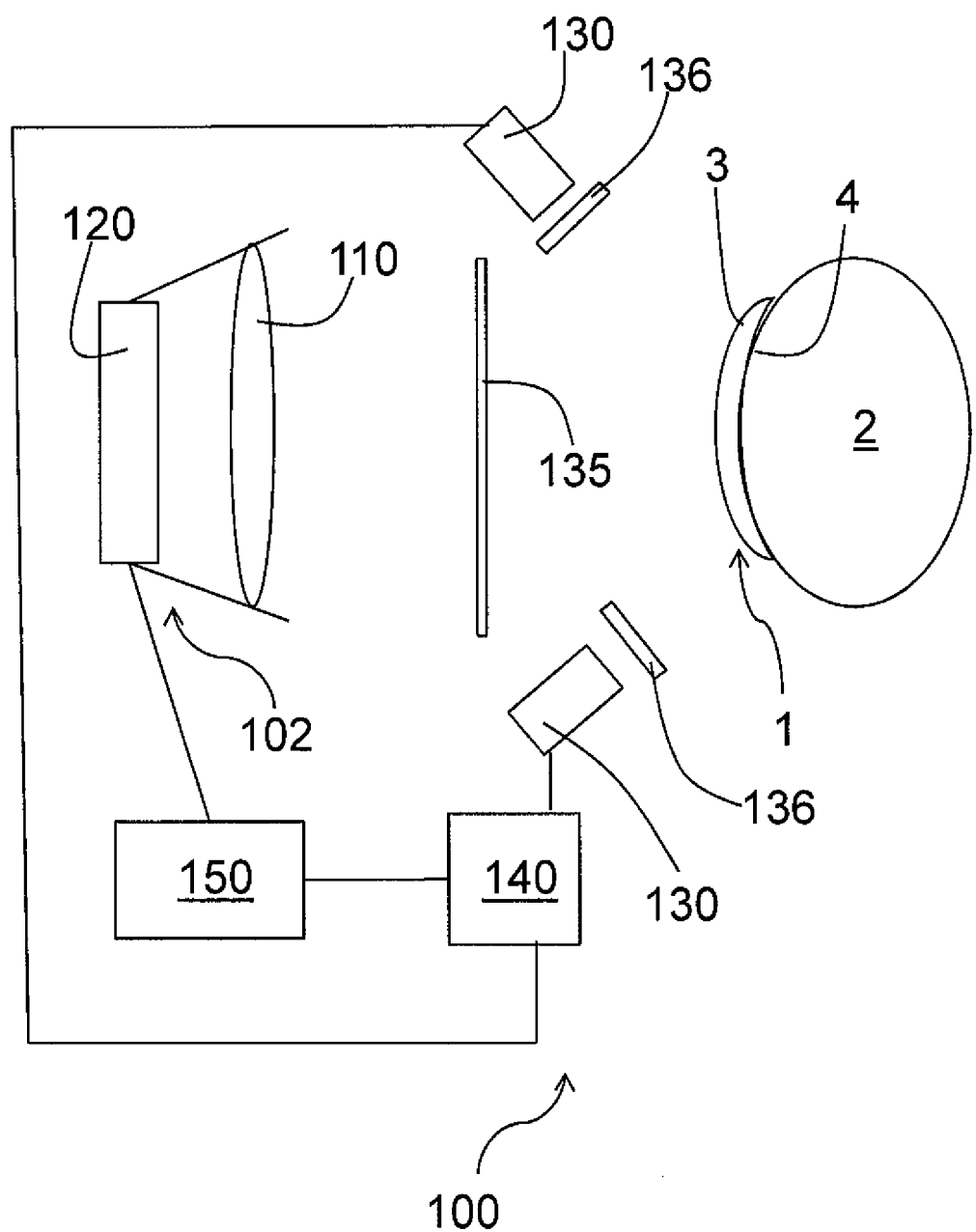
FIG. 3 a schematic representation of a measuring system according to the invention.

FIG. 3 shows an embodiment of a measuring system 100 according to the invention, having a sensor assembly 1 applied onto a surface 4 of an object 2 with a carrier 3. The sensor assembly 1 exhibits sensor elements 10, not shown here, arranged in a matrix-like fashion (see FIG. 1), wherein each sensor element 10 comprises at least one first sensor sub-element 15 (see FIGS. 2a, 2b, 2c), transparent for at least one wavelength region of light, and at least one second sensor sub-element 11, 12, 13 (see FIGS. 2a, 2b, 2c), sensitive to at least one variable. More specific configurations of the sensor assembly 1 can be found for example in the FIGS. 1, 2a, 2b, 2c.

The measuring system 100 has a detection system 102 and an illumination system 130. The illumination system 130 may for example comprise LEDs, OLEDs, lasers, or various lamps as light source. It may also be conceived of for the generation of light in the illumination system to be based on a luminescence effect. The detection system 102 exhibits a detector 120 and an imaging optics 110. Advantageously, as indicated in the figure, detector 120 and imaging optics 110 are protected against scattered light, so that they form a camera. In order to realise specific types of illumination, like continuous light, single pulses, or pulse sequences, the illumination system 130 is controlled by a control unit 140. Also controlled by the control unit 140 are an evaluation unit 150 and the detection system 102. The measuring system 100 may furthermore exhibit optical filters or filter systems 135 between the sensor assembly 1 and the detection system 102, as well as optical filters or filter systems 136 between the illumination system 130 and the sensor assembly 1. Both of the filters or filter systems 135, 136 may be switchable or controllable, so that for example the wavelength region of light, for which a filter or filter system 135, 136 is transparent, can be changed, preferentially under control by the control unit 140.

For example, in the measuring system 100 the sensor assembly 1 can be illuminated with a series of light pulses, under control by the control unit 140. The detection system 102 records at least one image of the sensor assembly 1 for each light pulse, furthermore at least one image of the object 2 is recorded through the first sensor sub-elements 15 of the sensor elements 10 of the sensor assembly 1. The recorded images of the sensor assembly 1 are evaluated in the evaluation unit 150 with respect to the distribution of at least one variable, and the result of the evaluation is processed by the evaluation unit 150 along with the image of the object 2 to generate a combined image.

Different embodiments of the method according to the invention for capturing the two-dimensional distribution of at least one variable of the object 2 in an image-like fashion may also be carried out with the measuring system 100.

Figure 4:
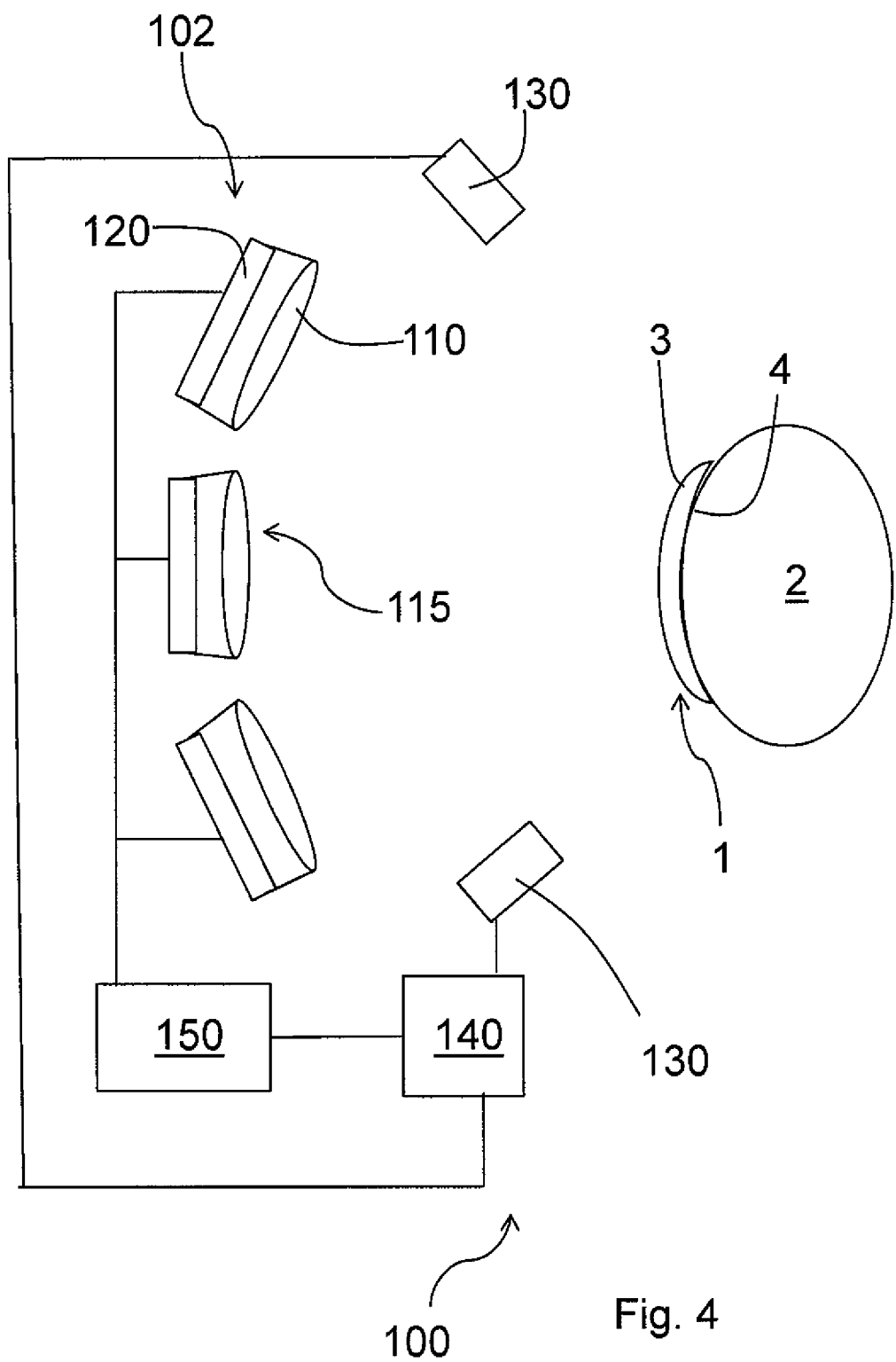
FIG. 4 a further embodiment of a measuring system according to the invention.

FIG. 4 shows a further embodiment of a measuring system 100 according to the invention. In contrast to the embodiment shown in FIG. 3, where the essential elements have already been described, the embodiment of the measuring system 100 of FIG. 4 exhibits a detection system 102 with plural cameras 115, here three, each comprising a detector 120 and a corresponding imaging optics 110. The detectors 120 therein may differ with respect to the wavelength region of light they are sensitive to. With an arrangement of the cameras 115 in the way shown, advantageously the different angles under which the cameras 115 are directed onto the sensor assembly 1 are compensated by the respective imaging optics 110 and/or by the evaluation unit 150. Only in this way can the recorded images be superposed for evaluation or visual presentation. Of course, in an embodiment of this type, also filters or filter systems as shown in FIG. 3 may be provided.

Figure 5:
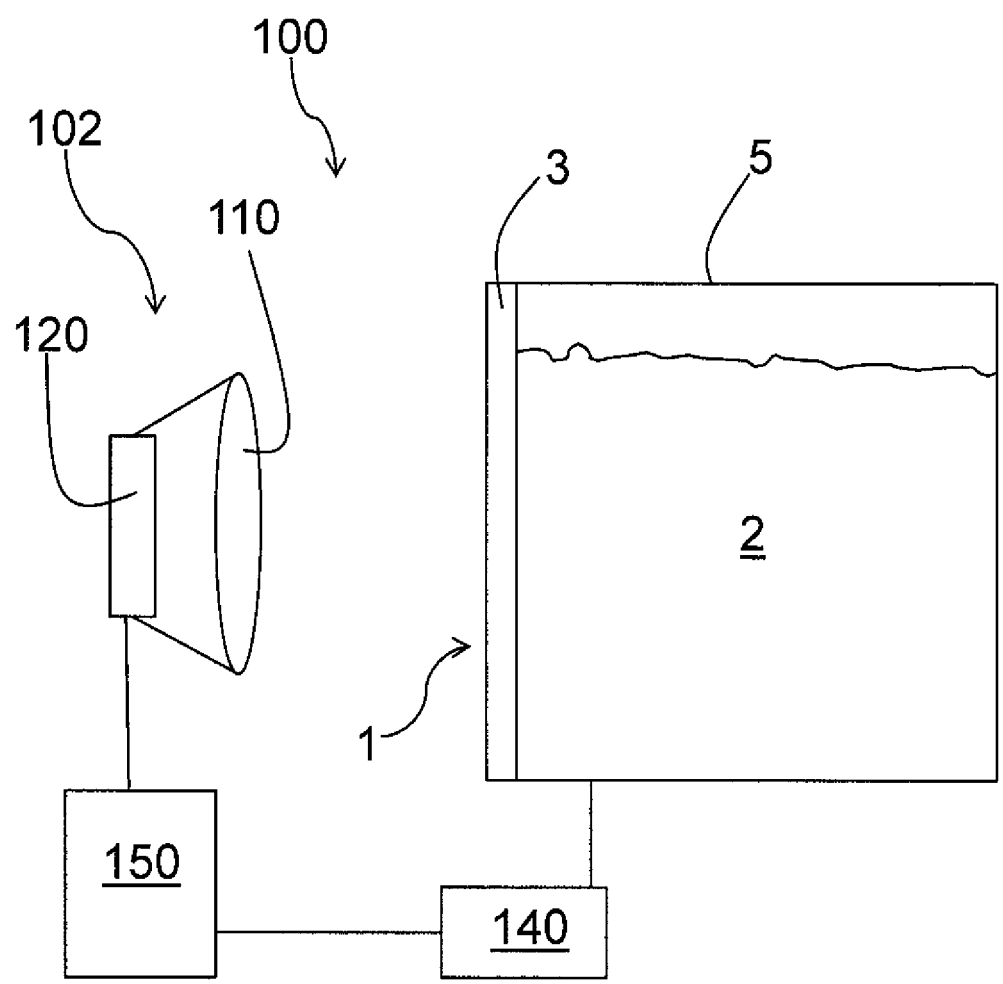
FIG. 5 a further embodiment of a measuring system according to the invention, in which the illumination is by luminescence.

FIG. 5 shows a further embodiment of a measuring system 100 according to the invention. The object 2 here is a liquid in a container 5. On the inside of the container 5 a sensor assembly 1 according to the invention is provided on a carrier 3. Images of the sensor assembly 1 and of the object 2 can be recorded by the detection system 102. The images can be processed by an evaluation unit 150, which is controlled by a control unit 140, analogously to the previously described embodiments. The illumination of the sensor assembly here is achieved by luminescence triggered in the object 2, i.e. in the liquid. In the figure it is indicated that in specific embodiments the triggering of the luminescence may also be controlled by the control unit 140. The luminescence effect used may for example be photoluminescence, chemiluminescence, or electroluminescence.

FIG. 6 shows a further embodiment of a sensor assembly 1 with a plurality of sensor elements 10. Contrary to the embodiment shown in FIG. 1, here the sensor assembly 1 is applied directly on a surface 4 of an object 2, a part of which is shown here. This is to say that a carrier 3 like in FIG. 1 is not used here. Just as in any other embodiment of the sensor assembly 1, however, it is not excluded that prior to applying the sensor assembly 1 onto the surface 4 of the object 2 the surface 4 of the object 2 is treated in a suitable fashion. For applying the sensor assembly 1 onto the surface 4 of the object 2 the sensor sub-elements 11, 12, 13 (see FIGS. 7a, 7b, 7c) of the sensor elements 10 can for example be applied separately onto the surface 4 according to the mode of operation of an ink-jet printer. In the sensor assembly 1 furthermore two reference marks 20 are provided, in analogy to the embodiment shown in FIG. 1.

FIG. 7a shows an embodiment of a sensor element 10 in the case of a sensor assembly 1 like in FIG. 6. The sensor element exhibits a second sensor sub-element 11 sensitive to at least one variable. The second sensor sub-element 11 here is of circular shape, which is not to be taken as a limitation of the invention. The statements with respect to shape and size of the sensor sub-elements made in the context of the FIGS. 2a, 2b, and 2c may be carried over to FIG. 7a, and likewise to FIGS. 7b and 7c. The sensor element 10 furthermore exhibits a first sensor sub-element transparent to at least one wavelength region of light. In the embodiment shown the first sensor sub-element is a region 17 of the surface 4 of the object 2 left uncovered during the application of the sensor elements 10.

FIG. 7b shows a further embodiment of a sensor element 10 for a sensor assembly 1 of the type described in FIG. 6. The sensor element 10 shows a first sensor sub-element transparent for at least one wavelength region of light. In the embodiment shown the first sensor sub-element is a region 17 left uncovered on the surface 4 of the object 2 during the application of the sensor elements 10. Furthermore the sensor element 10 exhibits two second sensor sub-elements 11, 12, each sensitive to at least one variable.

FIG. 7c shows a further embodiment of a sensor element 10 for a sensor assembly 1 of the type described in FIG. 6. The sensor element 10 exhibits a first sensor sub-element transparent for at least one wavelength region of light. In the embodiment shown the first sensor sub-element is a region 17 left uncovered on the surface 4 of the object 2 during the application of the sensor elements 10. Furthermore the sensor element 10 exhibits three second sensor sub-elements 11, 12, 13, each sensitive to at least one variable.

Figure 8:
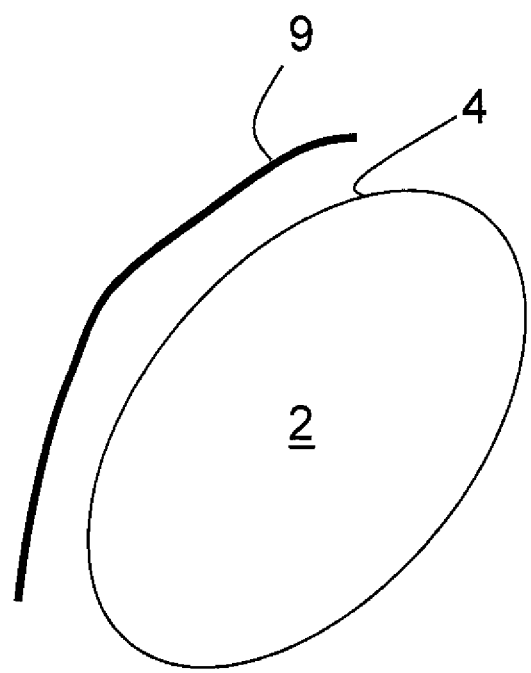
FIG. 8 a principle of applying the sensor assembly on an object.

FIG. 8 illustrates a possibility for applying the sensor elements 10 of a sensor assembly 1 of the type shown in FIG. 6 onto a surface 4 of an object 2. The sensor sub-elements, not shown here, of the sensor assembly 1 at first are provided on an intermediate medium 9, by means of which they are brought into contact with the surface 4 of the object 2. The sensor sub-elements therein are configured such that they stick more strongly to the surface 4 of the object than to the intermediate medium 9. The intermediate medium 9 is subsequently removed; therein the sensor sub-elements detach from the intermediate medium 9 and remain on the surface 4 of the object 2 in an arrangement which is largely determined by their prior arrangement on the intermediate medium 9.

The invention has been described with reference to specific, preferred embodiments. Alterations and modifications are possible, without leaving the scope of the subsequent claims.

What is claimed is:

1. A sensor assembly for capturing a distribution of at least one variable of an object in an image-like fashion comprising:
   a plurality of sensor elements arranged together in a matrix-like fashion in a two-dimensional area including a plurality of rows and/or columns of the sensor elements, each of the sensor elements having at least two corresponding sensor sub-elements including at least a first sensor sub-element and a second sensor sub-element exhibiting fixed positions with respect to the sensor assembly, wherein each first sensor sub-element is transparent for at least one wavelength region of light, and wherein each second sensor sub-element is sensitive to the at least one variable of the object,
   wherein the at least one variable of the object is a concentration of a substance, or a partial pressure of a substance, or a pH-value of the object, or the presence of a substance, or a physical quantity, wherein an optical behavior of each second sensor sub-element is determined by the at least one variable of the object, and wherein the optical behavior is a change of color or a luminescence effect that is generated by each second sub-sensor element across the two-dimensional area such that the optical behavior is capturable by an image detector to generate a recorded image of the distribution of the at least one variable in the image-like fashion across the two-dimensional area.

2. The sensor assembly as recited in claim 1 wherein the first sensor sub-element of each sensor element is sensitive to at least one variable of the object.

3. The sensor assembly as recited in claim 1 wherein each sensor element has at least one first sensor sub-element and at least two second sensor sub-elements, wherein the at least two second sensor sub-elements differ with respect to at least one variable of the object to which they are sensitive.

4. The sensor assembly as recited in claim 1 wherein the physical quantity is temperature or pressure.

5. The sensor assembly as recited in claim 1 wherein each sensor element is localised on a carrier.

6. The sensor assembly as recited in claim 5 wherein first sensor sub-element of each sensor element comprises an opening in the carrier.

7. The sensor assembly as recited in claim 5 wherein the first sensor sub-element of each sensor element comprises a material transparent for the at least one wavelength region of light, or is an uncovered region on the carrier, corresponding to the second sensor sub-element of each sensor element.

8. The sensor assembly as recited in claim 5 wherein the carrier is a plastic sheet.

9. The sensor assembly as recited in claim 1 wherein the sensor elements of the sensor assembly are applied to the object without a carrier.

10. The sensor assembly as recited in claim 9 wherein the first sensor sub-element of each sensor element is a region, corresponding to the second sensor sub-element of each sensor element, and left uncovered during application of the sensor elements on a surface of the object.

11. The sensor assembly as recited in claim 1 wherein at least two sensor elements differ with respect to their respective sensor sub-elements.

12. The sensor assembly as recited in claim 11 wherein a first area of the sensor assembly exhibits sensor elements which differ with respect to their respective sensor sub-elements from the sensor elements in a second area of the sensor assembly.

13. The sensor assembly as recited in claim 11 wherein sensor sub-elements sensitive to a common variable of the object and belonging to different sensor elements differ in their cross-sensitivity to at least one respectively further variable of the object.

14. The sensor assembly as recited in claim 1 wherein reference marks are provided in the sensor assembly for facilitating alignment of a captured image of the sensor assembly during evaluation.

15. A method for capturing the two-dimensional distribution of at least one variable of an object in an image-like fashion, comprising the following steps:
 a) applying a sensor assembly on a surface of the object, wherein the sensor assembly has a plurality of sensor elements arranged in a matrix-like fashion to define a two-dimensional area including a plurality of rows and/or columns of the sensor elements, and wherein each sensor element includes at least one first sensor sub-element transparent for at least one wavelength region of light, and includes at least one second sensor sub-element, which is sensitive to at least one variable of the object, the at least one variable of the object being a concentration of a substance, or a partial pressure of a substance, or a pH-value of the object, or the presence of a substance, or a physical quantity;
 b) illuminating the sensor assembly with light from at least one wavelength region of light to generate an optical behavior of the second sensor sub-elements along the two-dimensional area, the optical behaviour being determined by the at least one variable of the object, the optical behavior being a change of color or a luminescence effect;
 c) recording at least one image of the optical behaviour of the second sensor sub-elements of the sensor assembly in response to the illumination, the sensor response representing the two-dimensional distribution of the at least one variable of the object across the two-dimensional area;
 d) recording at least one image of the surface of the object across the two-dimensional area through the first sensor sub-elements; and
 e) generating at least one combined image from the images recorded in the steps c and d by superposing the optical behaviour of the second sensor sub-elements on the surface of the object across the two-dimensional area.

16. The method as recited in claim 15 wherein the sensor assembly is illuminated with a light pulse from at least one wavelength region of light, and a plurality of images are recorded in succession according to step c.

17. The method as recited in claim 15 wherein the sensor assembly is illuminated with a plurality of light pulses in succession, wherein each light pulse is from respectively at least one wavelength region of light, and wherein, for each light pulse, at least one image of the sensor assembly according to step c is recorded.

18. The method as recited in claim 15 wherein the sensor assembly is illuminated with continuous illumination.

19. The method as recited in claim 15 wherein applying the sensor assembly on the surface of the object is accomplished by applying the individual sensor sub-elements.

20. The method as recited in claim 15 wherein applying a sensor assembly to the surface of the object is accomplished by applying a carrier exhibiting the sensor elements on the surface of the object.

21. The method as recited in claim 15 wherein applying the sensor assembly on the surface of the object is accomplished by bringing an intermediate medium, carrying the sensor elements, into contact with the surface of the object, the sensor elements sticking to the surface of the object, and removing the intermediate medium prior to recording images, wherein the sensor elements detach from the intermediate medium.

22. A measuring system for capturing the two-dimensional distribution of at least one variable of an object in an image-like fashion, comprising:
 a detection system;
 an illumination system;
 an evaluation unit; and
 a sensor assembly with sensor elements arranged in a matrix-like fashion to define a two-dimensional area including a plurality of rows and/or columns of the sensor elements, wherein each sensor element includes at least one first sensor sub-element, transparent for at least one wavelength region of light, and includes at least one second sensor sub-element, which is sensitive to at least one variable of the object, the at least one variable of the object being a concentration of a substance, or a partial pressure of a substance, or a pH-value of the object, or the presence of a substance, or a physical quantity, and wherein the sensor assembly is configured to be applied on the object, the sensor assembly and the object illuminable with light from at least one wavelength region to generate an optical behavior of the second sensor sub-elements along the two-dimensional area, the optical behaviour being determined by the at least one variable of the object, the optical behavior being a change of color or a luminescence effect, and the detection system is configured to record:
- at least one first image of the optical behaviour of the second sensor sub-elements of the sensor assembly in response to the illumination, the sensor response representing the two-dimensional distribution of the at least one variable of the object across the two-dimensional area, and
- at least one second image of the object across the two-dimensional area through the first sensor sub-elements, the evaluation unit configured for generating at least one combined image from the recorded at least one first image and the recorded at least one second image by superposing the optical behaviour of the second sensor sub-elements on the surface of the object across the two-dimensional area.

23. The measuring system as recited in claim 22 wherein the detection system comprises at least one detector and corresponding imaging optics, wherein each detector is sensitive in at least one wavelength region of light.

24. The measuring system as recited in claim 23 wherein light from a wavelength region of light in which the sensitivity regions of a detector overlap is suppressed by an optical notch filter.

25. The measuring system as recited in claim 22 wherein the illumination system is based on a luminescence effect.

26. A sensor assembly for capturing the distribution of at least one variable of an object in an image-like fashion comprising:

- a plurality of sensor elements arranged together in a matrix-like fashion in a two-dimensional area including a plurality of rows and/or columns of the sensor elements, each of the sensor elements having at least one first sensor sub-element and at least two second sensor sub-elements, wherein the at least two second sensor sub-elements of each sensor differ with respect to at least one variable of the object to which they are sensitive;
- each of the corresponding sensor sub-elements exhibiting fixed positions with respect to the sensor assembly, wherein each first sensor sub-element is transparent for at least one wavelength region of light, and wherein each of the second sensor sub-elements are sensitive to at least one variable of the object,
- wherein the at least one variable of the object is a concentration of a substance, or a partial pressure of a substance, or a pH-value of the object, or the presence of a substance, or a physical quantity, wherein an optical behavior of the at least two second sensor sub-elements is determined by the at least one variable of the object, and wherein the optical behavior is a change of color or a luminescence effect that is generated by each second sub-sensor element across the across the two-dimensional area such that the optical behavior is capturable by an image detector to generate a recorded image of the distribution of the at least one variable in the image-like fashion across the two-dimensional area.

27. The sensor assembly as recited in claim 26, wherein each sensor element is made of one first sensor sub-element and at least three second sensor sub-elements.

28. The sensor assembly as recited in claim 26, wherein each sensor element is made of one first sensor sub-element and four second sensor sub-elements.

* * * * *